US00PP26045P3

(12) United States Plant Patent
Schoone

(10) Patent No.: US PP26,045 P3
(45) Date of Patent: Nov. 3, 2015

(54) ***PHALENOPSIS* ORCHID PLANT NAMED 'OLIVIA'**

(50) Latin Name: *Phalaenopsis hybrida*
Varietal Denomination: Olivia

(71) Applicant: René Schoone, Assendelft (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 191 days.

(21) Appl. No.: 13/986,340

(22) Filed: Apr. 23, 2013

(65) Prior Publication Data

US 2013/0291259 P1 Oct. 31, 2013

Related U.S. Application Data

(60) Provisional application No. 61/638,126, filed on Apr. 25, 2012.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Anne Grunberg
(74) *Attorney, Agent, or Firm* — Foley & Lardner LLP; Sunit Talapatra

(57) ABSTRACT

A new and distinct *Phalaenopsis* plant named 'Olivia' particularly characterized by flowers which are white with a purple/violet haze and purple/violet stripes and a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Olivia'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Olivia'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Olivia' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Olivia' originated from a cross made by the inventor in 1999 in Strengweg, Heemskerk, The Netherlands. The female or seed parent is the *Phalaenopsis* cultivar designated 'Little Hatter', unpatented. The male or pollen parent is the *Phalaenopsis* cultivar designated 'Little Gem Stripes', unpatented. The new *Phalaenopsis* 'Olivia' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Olivia', which in combination distinguish this *Phalaenopsis* as a new and distinct cultivar:

1. flowers which are white with a purple/violet haze and purple/violet stripes and a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Olivia', the female parent 'Little Hatter' has white flowers with a red labellum and the male parent 'Little Gem Stripes' has light pink striped flowers and a purple labellum, whereas the flowers of 'Olivia' are white with a purple/violet haze and purple/violet stripes and a purple labellum.

Presently, the commercial cultivar to which 'Olivia' can be meaningfully compared is 'Submarine' (unpatented). The size of the plant of 'Olivia' is a little smaller and also the flower of 'Olivia' is a little smaller than the flower of 'Submarine'. The color of the sepals and petals of 'Submarine' is darker purple than the color of 'Olivia' and also differs the shape of the labellum.

BRIEF DESCRIPTION OF THE PHOTOGRAPHS

The accompanying photographs illustrate the overall appearance of the new *Phalaenopsis* 'Olivia' showing the colors as true as is reasonably possible with colored reproductions of this type. Colors in the photographs may differ slightly from the color values cited in the detailed botanical description, which accurately describe the color of 'Olivia'.

DETAILED BOTANICAL DESCRIPTION

Figure 1:
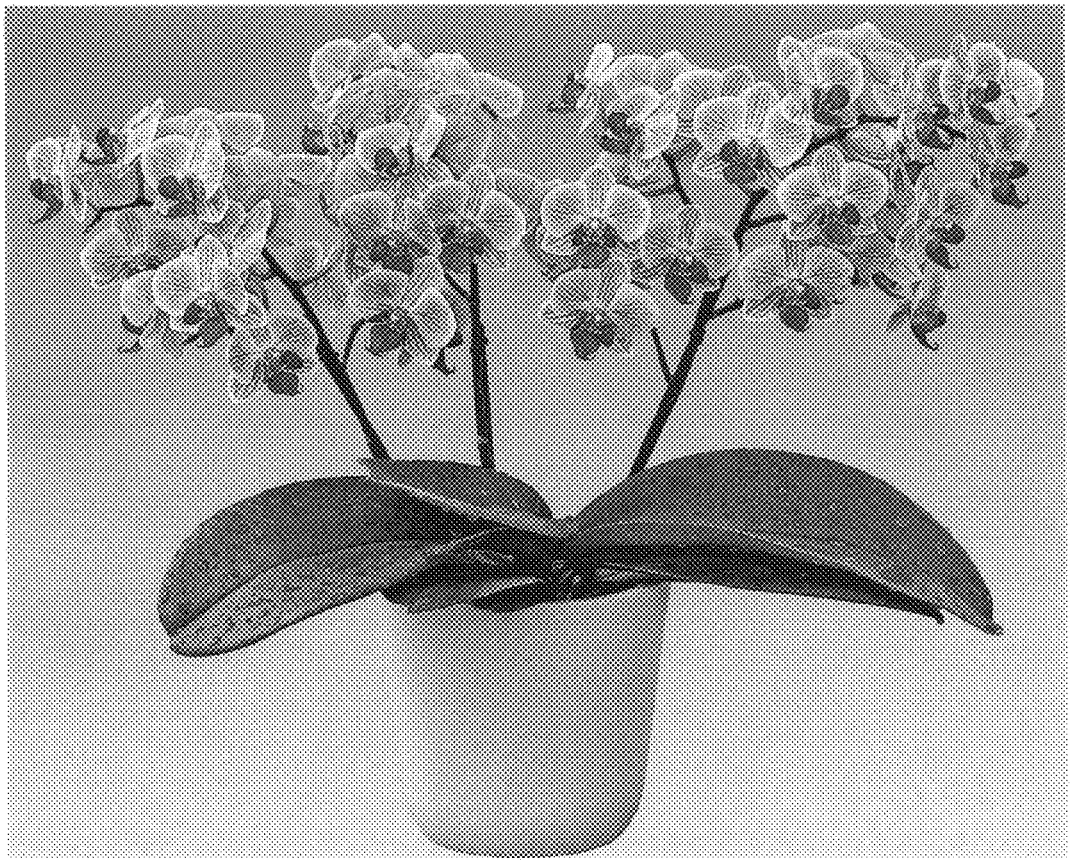
FIG. 1 shows a side view perspective of a typical flowering plant of 'Olivia' in a 12 cm pot, at 16 months of age.

The new *Phalaenopsis* cultivar 'Olivia' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Olivia' as grown in a greenhouse in Strengweg, Heemskerk, The Netherlands, under conditions which closely approximate those generally used in commercial practice. Initially, the ideal temperature to grow plants of 'Olivia' is 27° C. during the day and at night. Then, during the flowering phase of 'Olivia', the ideal growing temperature is 20-22° C. during the day and 18° C. at night. Light levels for growing 'Olivia' are a minimum of 5,000 lux and a maximum of 10,000 lux. A balanced fertilizer with level of 200 ppm N, 87 ppm P, 168 ppm K is applied. Duration of growth of 'Olivia' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Olivia' plants described is 12 months after potting.

Classification:

*Botanical.*—*Phalaenopsis hybrida.*

Parentage:

*Female or seed parent.*—*Phalaenopsis* cultivar designated 'Little Hatter', unpatented.

*Male or pollen parent.*—*Phalaenopsis* cultivar designated 'Little Gem Stripes', unpatented.

Propagation:

*Type.*—Tissue culture.

*Rooting habit and description.*—Fleshy; approximately 4 mm-7 mm wide and green in color (RHS 144A and RHS 148C); freely branching. It takes 12 weeks for plants growing in tissue culture to initiate roots.

Plant:

*Size at maturity.*—Height (from bottom of pot to highest flower): about 35 cm to 40 cm. Spread: about 30 cm to 40 cm.

*Growth habit.*—Small; dark green leaves (RHS 137B) and a relatively large raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip blunt and asymmetric.

*Texture* (*upper & underside*).—Smooth and leathery.

*Pubescence.*—None.

*Mature leaf length.*—About 15 to 20 cm.

*Mature leaf width.*—About 8 cm.

*Mature leaf thickness.*—About 1.5 mm.

*Mature leaf color.*—Upper side: green (RHS 137B). Under side: yellow/green (RHS 146B).

*Leaf base.*—Acute.

*Margin.*—Entire.

*Venation.*—Pattern: parallel. Color of midvein: upper side: green (RHS 137A). Under side: yellow/green (RHS 146A).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 3.

*Number of flowers per raceme.*—About 10 to 25.

*Length.*—About 25 to 35 cm.

Peduncle:

*Diameter.*—About 3 mm.

*Strength.*—Strong.

*Aspect.*—Upright.

*Texture.*—Glabrous and smooth.

*Color.*—Purple (RHS N77A) with yellow/green (RHS 144A).

Buds:

*Height* (*from base to tip*).—About 10 mm to 15 mm.

*Diameter* (*at midpoint*).—About 10 mm to 15 mm.

*Shape.*—Egg-shaped/oval.

*Color.*—Main color is yellow/green (RHS 149B) with purple stripes and a purple haze (RHS N77B).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening.*—Flowers fully opened about 2 to 3 days after petal and sepal separation.

*Orientation at opening.*—Slanted upward and outward.

Figure 2:
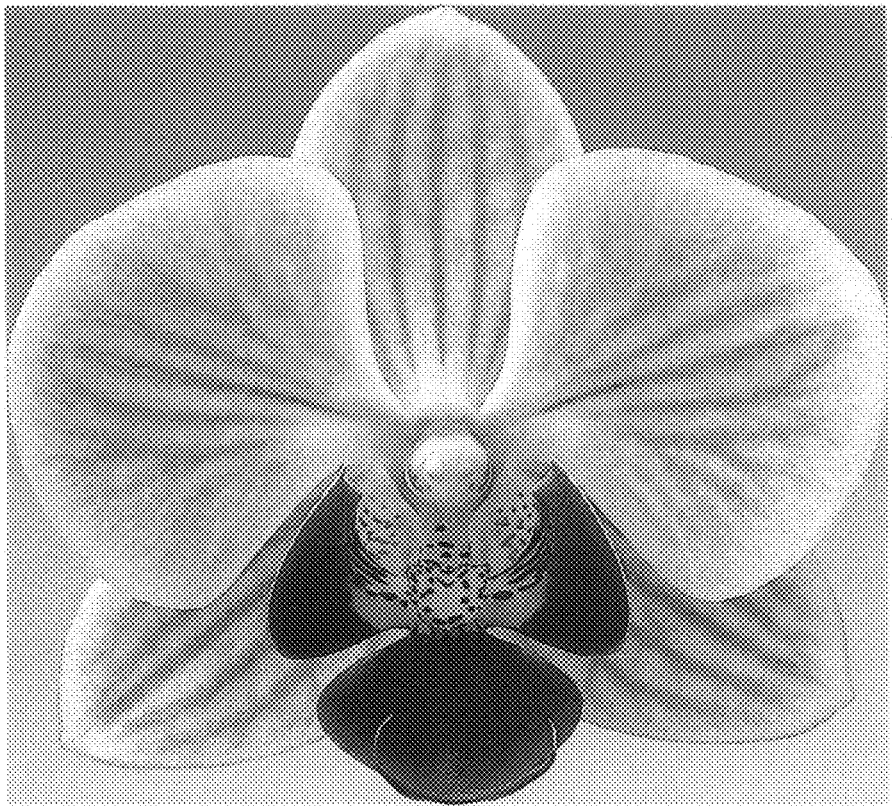
FIG. 2 shows a close-up view of the typical flower of 'Olivia'.
Figure 3:
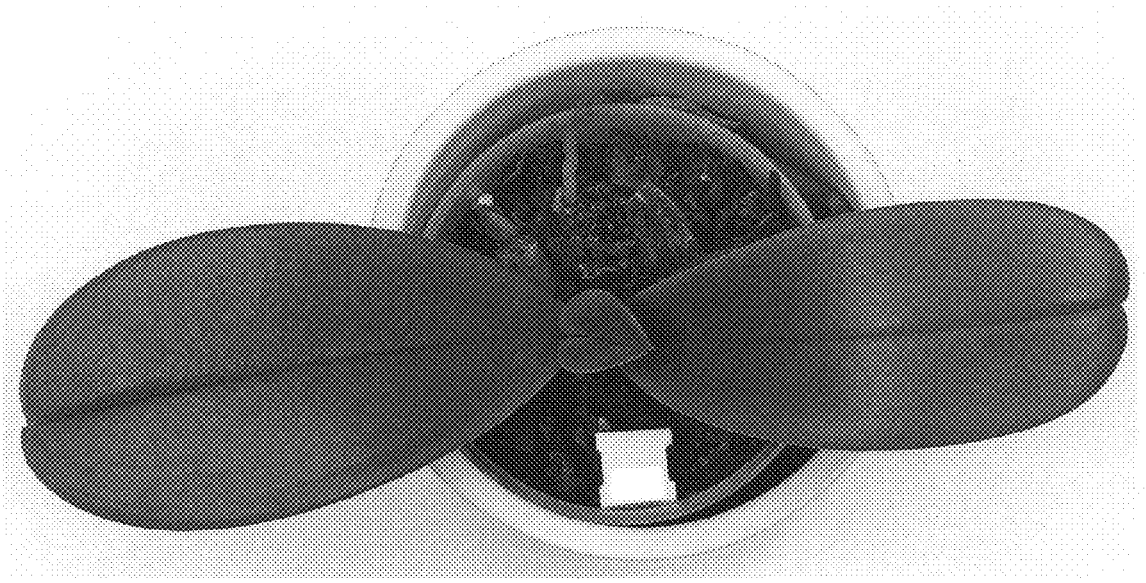
FIG. 3 shows a close-up view of the typical leaves of 'Olivia'.

*Shape.*—Typical Shape of *Phalaenopsis* Orchid; see FIG. 2.

*Size.*—Height: about 40 to 50 mm. Diameter: about 45 to 55 mm.

*Quantity and arrangement.*—Three petals and three sepals that are trimerous, overlapping and arranged in 2 whorls. Petals are more pronounced than sepals.

Petals:

*Arrangement.*—Inner whorl comprises 3 petals: 2 lateral petals and labellum.

2 *Lateral petals.*—Overall shape: little triangular and weakly cupped. Apex: round/oval. Margin: entire and weakly undulate. Base: broadly ovate. Length: about 26 mm. Width: about 25 mm. Texture: Upper surface: smooth and satiny. Under surface: smooth and satiny. Color (when fully opened): upper side: edges are white (RHS NN155B). Veins are purple/violet (RHS N80A) and a purple/violet haze (RHS N80C). Under side: edges are white (RHS NN155B). At the base white (RHS NN155B) with purple/violet (RHS N80D) and a purple haze (RHS N80C). Middle vein is purple/violet (RHS N80A). The other stripes are (RHS N80B and RHS N80C).

*Labellum.*—Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: Entire and weakly undulate. Apex: Oval. Length: About 18 mm. Width (not flattened): About 15 mm. Depth of tube created by lateral lobes of labellum: About 8 mm. Texture: Upper and under surface: Smooth and satiny. Color (when fully opened): Midlobe: upper surface: main color is purple (RHS N79B) which runs into purple at the edges and the cirrhi (RHS N81A). At the base some white (RHS NN155B) and yellow/orange (RHS 15A). Under surface: Main color is white (RHS NN155B). Outer edges are purple (RHS N81A) which runs into RHS N79C. At the base some yellow (RHS 12A). Lateral lobs: upper surface: main color is purple (RHS N79B). At the base some white (RHS NN155C). At the end purple (RHS N81A). Under surface: at the base grey/purple (RHS N187D) which runs into RHS N187C) and into purple (RHS N79C) with a small white edge (RHS NN155B).

*Cirrhi.*—About 8 mm (middle). Color: purple (RHS N79C) which runs into white (RHS NN155B).

*Pestle* (*callosities*).—Length: about 4 mm. Width (not flattened): about 3 mm. Color: sides are white (RHS NN155C), the edges and inside are yellow/orange (RHS 14A) with a purple spots (RHS N79A).

Sepals:

*Arrangement.*—Outer whorl comprises 3 sepals, one dorsal and two lateral sepals.

*Overall shape.*—Oval; dorsal sepal is weakly cupped.

*Margin.*—entire and weakly undulate.

*Length.*—about 24 mm.

*Width.*—about 15 mm.

*Apex.*—oval and little pointy.

*Texture.*—Upper and under surface: smooth and satiny.

*Color* (*when fully opened*).—upper surface: Dorsal: The main color is purple (RHS N80C) the edges are white (RHS NN155B) the stripes and veins are purple (RHS N80A). Lateral: The main color is white (RHS NN155B). Stripes are purple (RHS N80A) and a purple haze (RHS N80C). At the base yellow/green mark (RHS 154D) with purple spots (RHS N80A). Underside: Dorsal: edges are white (RHS NN155D) with vague purple stripes (RHS 77A) and a purple haze (RHS 77C). Lateral: Main color is white (RHS NN155D). Vague purple stripes (RHS 77A) and a purple haze (RHS 77C). At the base a vague yellow/green mark (RHS 151D).

Pedicel:

*Length.*—About 30 mm.

*Diameter.*—About 3 mm.

*Texture.*—Glabrous and smooth.

*Color.*—From purple (RHS N77A) to purple (RHS 77C) with a yellow/green haze (RHS 145B).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 9 mm. Diameter: about 3 mm. Color: purple/violet (RHS N80B) and white (RHS NN155B).

*Pollinia.*—Quantity: two. Diameter: about 1 mm. Color: orange (RHS 24A).

*Ovary.*—Length: about 3 mm. Diameter: about 4 mm. Color: white (RHS NN155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Olivia', as illustrated and described herein.

* * * * *

UNITED STATES PATENT AND TRADEMARK OFFICE

CERTIFICATE OF CORRECTION

PATENT NO. : PP26,045 P3
APPLICATION NO. : 13/986340
DATED : November 3, 2015
INVENTOR(S) : René Schoone It is certified that error appears in the above-identified patent and that said Letters Patent is hereby corrected as shown below:

ON THE TITLE PAGE, Item (71) should read:

(71) Applicant: Floricultura, Heemskerk (NL)

ON THE TITLE PAGE, Item (30) should read:

(30) Foreign Application Priority Data

Apr. 26, 2012 (NL) .....OPS898

Signed and Sealed this
Ninth Day of February, 2016

Michelle K. Lee

Michelle K. Lee
*Director of the United States Patent and Trademark Office*